United States Patent [19]

Trummlitz et al.

[11] 4,447,434

[45] May 8, 1984

[54] SUBSTITUTED DIBENZODIAZEPINONES

[75] Inventors: Günter Trummlitz, Warthausen; Wolfhard Engel, Biberach; Wolfgang Eberlein, Biberach; Günther Schmidt, Biberach, all of Fed. Rep. of Germany; Rudolf Hammer, Milan; Piero del Soldato, Monza, both of Italy

[73] Assignee: Dr. Karl Thomae GmbH, Biberach an der Riss, Fed. Rep. of Germany

[21] Appl. No.: 462,149

[22] Filed: Jan. 31, 1983

[30] Foreign Application Priority Data

Feb. 6, 1982 [DE] Fed. Rep. of Germany ....... 3204157

[51] Int. Cl.³ .................. C07D 403/06; A61K 31/55
[52] U.S. Cl. .................................. 424/256; 424/263; 424/267
[58] Field of Search .............. 260/239.3 T; 424/267, 424/263, 256

[56] References Cited

U.S. PATENT DOCUMENTS 4,377,576 3/1983 Schmidt et al. .............. 260/239.3 T Primary Examiner—Robert T. Bond
Attorney, Agent, or Firm—Hammond & Littell, Weissenberger & Dippert

[57] ABSTRACT

The specification describes new substituted dibenzodiazepinones of formula

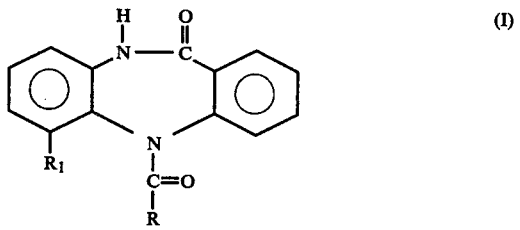

wherein $R_1$ is hydrogen or chlorine atom and R is (1-methyl-4-piperidinyl)methyl, (1-methyl-1,2,5,6-tetrahydro-4-pyridinyl)methyl, 1-methyl-1,2,5,6-tetrahydro-4-pyridinyl, (1-methyl-4-piperidinylidene)methyl, (2,3-dehydro-8-methyl-8-aza-bicyclo[3,2,1]oct-3-yl)-methyl, (8-methyl-8-aza-bicyclo[3,2,1]oct-3-ylidene)-methyl or an endo-or exo-(8-methyl-8-azabicyclo[3,2,1]oct-3-yl)methyl each being optionally substituted by one or two methyls on the heterocyclic ring, and the nontoxic, pharmaceutically acceptable acid addition salts thereof, processes for preparing them and pharmaceutical compositions containing these compounds.

The compounds of formula I have an antiulcerative effect and an inhibitory effect on the secretion of gastric substances having anticholinergic activity, such as dryness of the mouth and mydriasis.

11 Claims, No Drawings

SUBSTITUTED DIBENZODIAZEPINONES

BACKGROUND OF THE INVENTION

The invention relates to new substituted dibenzodiazepinones, processes for the preparation thereof and pharmaceutical compositions containing these compounds.

In German Offenlegungsschrift DE-OS No. 1 795 176, specific dibenzodiazepinones having an ulcer inhibiting and secretion inhibiting activity are described. From U.S. Pat. No. 3,953,430, substituted dibenzodiazepines with an antidepressant and analgesic activity are known.

OBJECTS OF THE INVENTION

It is an object of the invention to provide novel substituted dibenzodiazepinones and the nontoxic, pharmaceutically acceptable salts thereof.

It is another object of the invention to provide substituted dibenzodiazepinones and the nontoxic, pharmaceutically acceptable salts thereof which are useful in the prevention and treatment of disorders of the stomach and intestines such as inhibiting ulcers and inhibiting secretions as well as having antidepressant and analgesic activity.

Another object of the invention is to provide suitable intermediates for use in the preparation of the novel substituted dibenzodiazepinones.

A further object of the invention is to provide substituted dibenzodiazepinones of the formula

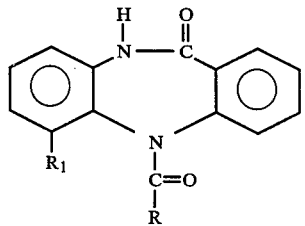

wherein $R_1$ is hydrogen or chlorine and R (1-methyl-4-piperidinyl)methyl, (1-methyl-1,2,5,6-tetrahydro-4-pyridinyl) methyl, 1-methyl-1,2,5,6-tetrahydro-4-pyridinyl, (1-methyl-4-piperidinylidene)methyl, (2,3-dehydro-8-methyl-8-azabicyclo[3,2,1]oct-3-yl)-methyl, (8-methyl-8-aza-bicyclo[3,2,1,]oct-3-ylidene)-methyl or an endo- or exo-(8-methyl-8-azabicyclo[3,2,1]oct-3-yl)methyl, each being optionally substituted by one or two further methyls on the heterocyclic ring, the diastereomeric and enantiomeric forms thereof and the nontoxic, pharmaceutically acceptable acid addition salts thereof with inorganic or organic acids.

These and other objects of the invention will become more apparent as the description thereof proceeds.

DESCRIPTION OF THE INVENTION

Dibenzodiazepinones with novel aminoacyl groups have now been found which have valuable pharmacological effects superior to those of the compounds mentioned above.

The invention relates to:

(a) substituted dibenzodiazepinones of formula I

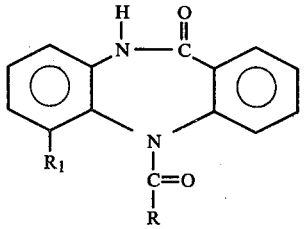

wherein $R_1$ is hydrogen or chlorine and R is (1-methyl-4-piperidinyl)methyl, (1-methyl-1,2,5,6-tetrahydro-4-pyridinyl)methyl, 1-methyl-1,2,5,6-tetrahydro-4-pyridinyl, (1-methyl-4-piperidinylidene)methyl, (2,3-dehydro-8-methyl-8-aza-bicyclo[3,2,1]oct-3-yl)-methyl, (8-methyl-8-azabicyclo[3,2,1]oct-3-ylidene)methyl, or the endo or exo-(8-methyl-8-azabicyclo[3,2,1]oct-3-yl)methyl group—each group being optionally substituted by one or two further methyl groups in the heterocyclic six-membered ring—and the acid addition salts thereof.

The compounds of formula I may also be obtained in the form of their nontoxic, pharmaceutically acceptable salts after being reacted with inorganic or organic acids. Suitable acids include, for example, hydrochloric, hydrobromic, sulphuric, phosphoric, tartaric, fumaric, citric, maleic, succinic, gluconic, malic, p-toluenesulfonic, methanesulfonic or amido-sulfonic acid.

The following compounds may be mentioned by way of example to illustrate the invention:

5,10-dihydro-5-[(1-methyl-4-piperidinyl)acetyl]-11H-dibenzo[b,e][1,4]diazepin-11-one 5,10-dihydro-5-[(1,3-dimethyl-4-piperidinyl)acetyl]-11H-dibenzo[b,e][1,4]diazepin-11-one 5,10-dihydro-5-[(1,2-dimethyl-4-piperidinyl)acetyl]-11H-dibenzo[b,e][1,4]diazepin-11-one cis-5,10-dihydro-5-[(1,2-dimethyl-4-piperidinyl)acetyl]-11H-dibenzo[b,e][1,4]diazepin-11-one trans-5,10-dihydro-5-[(1,2-dimethyl-4-piperidinyl)acetyl]-11H-dibenzo[b,e][1,4]diazepin-11-one cis-5,10-dihydro-5-[(1,3-dimethyl-4-piperidinyl)acetyl]-11H-dibenzo[b,e][1,4]diazepin-11-one trans-5,10-dihydro-5-[(1,3-dimethyl-4-piperidinyl)acetyl]-11H-dibenzo[b,e][1,4]diazepin-11-one 5,10-dihydro-5-[(1-methyl-1,2,5,6-tetrahydro-4-pyridinyl)acetyl]-11H-dibenzo[b,e][1,4]diazepin-11-one 5,10-dihydro-5-[(1,2-dimethyl-1,2,5,6-tetrahydro-4-pyridinyl)acetyl]-11H-dibenzo[b,e][1,4]diazepin-11-one 5,10-dihydro-5-[(1,3-dimethyl-1,2,5,6-tetrahydro-4-pyridinyl)acetyl]-11H-dibenzo[b,e][1,4]diazepin-11-one 5,10-dihydro-5-[(1,5-dimethyl-1,2,5,6-tetrahydro-4-pyridinyl)acetyl]-11H-dibenzo[b,e][1,4]diazepin-11-one 5,10-dihydro-5-[(1,6-dimethyl-1,2,5,6-tetrahydro-4-pyridinyl)acetyl]-11H-dibenzo[b,e][1,4]diazepin-11-one 5,10-dihydro-5-[(1,2,6-trimethyl-1,2,5,6-tetrahydro-4-pyridinyl)carbonyl]-11H-dibenzo[b,e][1,4]diazepin-11one cis-5,10-dihydro-5-[(1,2,6,trimethyl-1,2,5,6-trtrahydro-4-pyridinyl)carbonyl]-11H-dibenzo[b,e][1,4]diazepin-11-one trans-5,10-dihydro-5-[(1,2,6-trimethyl-1,2,5,6-tetrahydro-4-pyridinyl)carbonyl]-11H-dibenzo[b,e][1,4]diazepin-11-one 5,10-dihydro-5-[(1-methyl-1,2,5,6-tetrahydro-4-pyridinyl)carbonyl]-11H-dibenzo[b,e][1,4]diazepin-11-one 5,10-dihydro-[(1,2-dimethyl-1,2,5,6-tetrahydro-4-pyridinyl)-carbonyl]-11H-dibenzo[b,e][1,4]diazepin-11-one 5,10-dihydro-5-[(1,3-dimethyl-1,2,5,6-tetrahydro-4-pyridihyl)-carbonyl]-11H-dibenzo[b,e][1,4]diazepin-11-one 5,10-dihydro-5-[(1,5-dimethyl-1,2,5,6-tetrahydro-4-pyridinyl)-carbonyl]-11H-dibenzo[b,e][1,4]diazepin-11-one 5,10-dihydro-5-[(1,6-dimethyl-1,2,5,6-tetrahydro-4-pyridinyl)-carbonyl]-11H-dibenzo[b,e][1,4]diazepin-11-one endo-5,10-dihydro-5-[(8-methyl-8-azabicyclo[3,2,1]oct-3-yl)-acetyl]-11H-dibenzo[b,e][1,4]diazepin-11-one exo-5,10-dihydro-5-[(8-methyl-8-azabicyclo[3,2,1]oct-3-yl)acetyl]-11H-dibenzo[b,e][1,4]diazepin-11-one 5,10-dihydro-5-[(1-methyl-4-piperidinylidene)acetyl]-11H-dibenzo[b,e][1,4]diazepin-11-one 6-chloro-5,10-dihydro-5-[(1-methyl-4-piperidinyl)acetyl]-11H-dibenzo[b,e][1,4]diazepin-11-one 6-chloro-5,10-dihydro-5-[(1-methyl-1,2,5,6-tetrahydro-4-pyridinyl)acetyl]-11H-dibenzo[b,e][1,4]diazepin-11-one 6-chloro-5,10-dihydro-5-[(1-methyl-1,2,5,6-tetrahydro-4-pyridinyl)carbonyl]-11H-dibenzo[b,e][1,4]diazepin-11-one endo-6-chloro-5,10-dihydro-5-[(8-methyl-8-azabicyclo[3,2,1]-oct-3-yl)acetyl]-11H-dibenzo[b,e][1,4-]diazepin-11-one exo-6-chloro-5,10-dihydro-5-[(8-methyl-8-azabicyclo[3,2,1]-oct-3-yl)acetyl]-11H-dibenzo[b,e][1,4-]diazepin-11-one 6-chloro-5,10-dihydro-5-[(1,3-dimethyl-1,2,5,6-tetrahydro-4-pyridinyl)carbonyl]-11H-dibenzo[b,e][1,4-]diazepin-11-one The invention further relates to (b) pharmaceutical compositions containing one or more dibenzodiazepinones of formula I.

For this, the compounds of formula I can be incorporated in a manner known per se in the conventional pharmaceutical forms, e.g. in solutions, suppositories, tablets, coated tablets, capsules or infusions. The daily dose for oral administration is generally between 0.01 and 5, preferably between 0.02 and 2.5, more particularly between 0.05 and 1.0 mg/kg of body weight, generally administered in the form of several, preferably from 1 to 3 individual doses to achieve the desired results.

The substituted dibenzodiazepinones of general formula I and the acid addition salts thereof have valuable properties which make them commercially viable, and are characterized in particular by an excellent protective effect on the stomach and intestines in warm-blooded animals; for example, they inhibit the formation of gastric ulcers. Moreover, they have a useful therapeutic range, thanks to their low toxicity and the absence of any significant side effects.

The excellent activity of the substituted dibenzodiazepinones of formula I and of their nontoxic, pharmaceutically, i.e. biologically, acceptable acid addition salts make it possible to use them in both human and veterinary medicine, for the treatment and prophylaxis of diseases based on disorders of the stomach or intestines. They may be used, for example, to treat acute and chronic gastric and duodenal ulcers, gastritis and gastric hyperacidity in humans and animals.

If the substituted dibenzodiazepinones of formula I according to the invention and/or the pharmacologically acceptable acid addition salts thereof are to be used to treat the diseases mentioned above, the pharmaceutical preparations may also contain one or more pharmacologically active components from other groups of medicaments, such as antacids, e.g. aluminium hydroxide or magnesium aluminate; secretion inhibitors, such as H$_2$ blockers, e.g. cimetidine or ranitidine; gastric and intestinal therapeutic agents, e.g. metoclopramide, bromoprid and tiaprid; tranquilizers such as benzodiazepines, for example diazepam and oxazepam; spasmolytics, e.g. bietamiverine, camylofine; anticholinergics, e.g. oxyphencyclimine and phencarbamide; glucocorticoids such as prednisolone, fluocortolone, and betamethasone; non-steroidal antiphlogistic agents such as arylacetic acids and arylpropionic acids, heteroarylacetic acids and heteroarylpropionic acids, benzothiazine carboxiamide dioxides, pyrazolidinediones, quinazolinones, e.g. ibuprofen, naproxen, diclogenac, fenbufen, flurbiprofen, indomethacin, lonazolac, sudoxicam, piroxicam, phenylbutazone, bumadizon-calcium, proquazone; local anaesthetics such as tetracaine and procaine; and optionally also enzymes, vitamins, amino acids, etc.

The invention further relates to:

(c) processes for preparing the substituted dibenzodiazepinones of formula

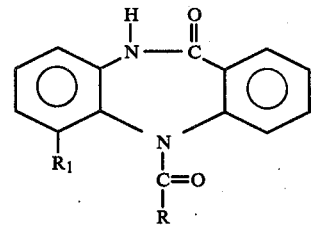

(I)

wherein R and R$_1$ are as hereinbefore defined, and the nontoxic, pharmaceutically acceptable acid addition salts thereof.

The compounds of formula I may be prepared as follows:

(a) All the compounds of formula I can be obtained by acylating dibenzodiazepinones of formula II

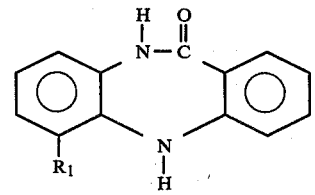

(II)

wherein R$_1$ is as hereinbefore defined, with acid derivatives of formula III

(III)

wherein R is as hereinbefore defined and Z represents a nucleophobic group or a leaving group.

The reaction of the compounds of formula II with the acid derivatives of formula III is effected in a manner known per se. The leaving group Z is a group which, together with the carbonyl group to which it is bonded, forms a reactive carboxylic acid derivative. Examples of reactive carboxylic acid derivatives include acid halides, esters, anhydrides or mixed anhydrides, as obtained from salts of the corresponding acid (Z=OH) and acid chlorides, such as phosphorus oxychloride, diphosphoric acid tetrachloride or chloroformates, or the N-alkyl-2-acyloxy-pyridinium salts formed by reacting compound III (Z=OH) with N-alkyl-2-halopyridinium salts.

The reaction is preferably carried out with the mixed anhydrides of strong inorganic acids, particularly dichlorophosphoric acid. The reaction is optionally carried out in the presence of an acid-binding agent (proton acceptor). Examples of suitable proton acceptors include alkali metal carbonates or alkali metal hydrogen carbonates, such as sodium carbonate or potassium hydrogen carbonate; tertiary organic amines, such as pyridine, triethylamine, ethyldiisopropylamine, 4-dimethylaminopyridine; or sodium hydride. The reaction is carried out at temperatures of between −25° and 130° C. in an inert solvent. Examples of suitable inert solvents include chlorinated aliphatic hydrocarbons such as methylene chloride or 1,2-dichloroethane; open-chained or cyclic ethers such as diethyl ether, tetrahydrofuran or 1,4-dioxan; aromatic hydrocarbons such as benzene, toluene, xylene or o-dichlorobenzene; polar aprotic solvents such as acetonitrile, dimethylformamide or hexamethylphosphoric acid triamide; or mixtures thereof. The reaction times are between 15 minutes and 80 hours, depending on the quantity and nature of the acylating agent of formula III used. It is not necessary to prepare the compounds of formula III in pure form; instead, they may be produced in situ in the reaction mixture in known manner.

(b) Compounds of formula I wherein R is (1-methyl-1,2,5,6-tetrahydro-4-pyridinyl-methyl or 1-methyl-1,2,5,6-tetrahydro-4-pyridinyl group, optionally substituted by one or two more methyl groups on the heterocyclic six-membered ring, are also obtained by reacting a dibenzodiazepinone of general formula II with acylating agents of formula IV

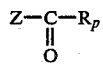    (IV)

wherein Z has the meanings given for formula III above and $R_p$ represents an optionally methyl-substituted or dimethyl-substituted 4-pyridinyl or (4-pyridinyl)methyl group.

Acylation will be successful under the conditions mentioned in (a), but it is preferably to carry out the reaction in boiling dioxan in the presence of pyridine, 4-dimethylamino-pyridine or triethylamine.

The intermediate compounds of formula

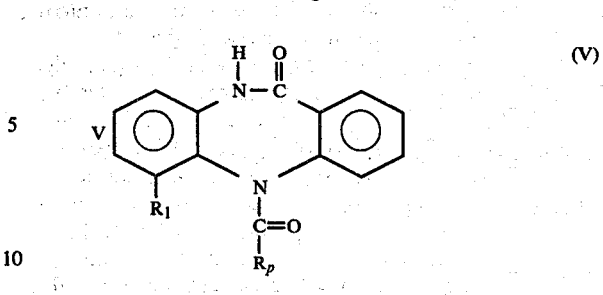

thus obtained, wherein $R_1$ and $R_p$ are as hereinbefore defined, are subsequently methylated with methylating agents of formula VI

    (VI)

wherein X represents the acid group of a strong oxyacid, for example of sulfuric, methylsulfuric, fluorosulfonic, trifluoromethanesulfonic, methanesulfonic, benzenesulfonic, p-toluenesulfonic, p-bromobenzenesulfonic or phosphoric acid or a halide, preferably chloride, bromide or iodide, to form pyridinium salts of formula Va

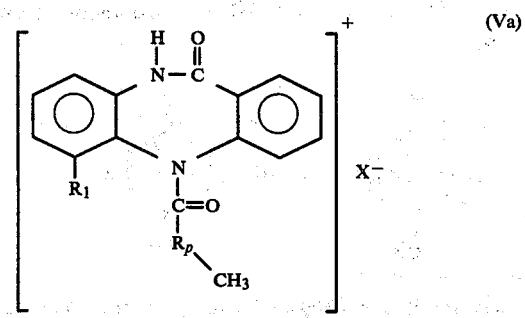

wherein $R_1$, $R_p$ and X are as hereinbefore defined. The methylation is carried out in inert solvents, e.g. chlorinated aliphatic hydrocarbons, such as methylene chloride, 1,2-dichloroethane, open-chained or cyclic ethers, such as diethyl ether or tetrahydrofuran, aromatic hydrocarbons, such as benzene, toluene, xylene or dichlorobenzene, but preferably in dioxan, acetonitrile or dimethylformamide and at temperatures of between −20° and +130° C., preferably between +30° and 100° C.

Subsequently reduction of the pyridinium salts Va with sodium or potassium borohydride or sodium or potassium alkoxy, dialkoxy or trialkoxyborohydride in protic solvents, for example in water, methanol, ethanol, 2-propanol or mixtures thereof at temperatures of between −40° and +50° C., preferably −5° to +10° C. produces the desired dibenzodiazepinones of formula I wherein $R_1$ has the meanings given hereinbefore and R is a (1-methyl-1,2,5,6-tetrahydro-4-pyridinyl)methyl or 1-methyl-1,2,5,6-tetrahydro-4-pyridinyl.

The processes for preparing the pharmacologically active dibenzodiazepinones of formula I are thus characterized in that dibenzodiazepinones of formula II are acylated with compounds of formula III or with pyridine alkanoic acid derivatives of formula IV, and then methylated and reduced with borohydrides or alkoxyborohydrides and optionally the resulting base is subsequently coverted into a nontoxic, pharmaceutically acceptable acid addition salt or an acid addition salt obtained is converted into the free base or a nontoxic, pharmaceutically acceptable acid addition salt.

(c) Compounds of formula I wherein R is (1-methyl-1,2,5,6-tetrahydro-4-pyridinyl)-methyl, (1-methyl-1,2,5,6-tetrahydro-4-piperidinylidene)-methyl, (2,3-dehydro-8-methyl-8-azabicyclo[3,2,1]oct-3-yl)-methyl or (8-methyl-8-aza-bicyclo[3,2,1]-oct-3-ylidene)-methyl group, each group being optionally substituted by one or two further methyl groups on the heterocyclic six-membered ring, can also be prepared by reacting a 5-dialkylphosphonoacetyldibenzodiazepinone of formula VII

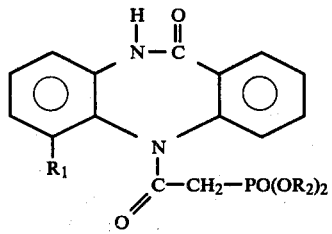

wherein $R_1$ is as hereinbefore defined and $R_2$ is alkyl of 1 to 10 carbon atoms, preferably an ethyl group, with a piperidinone of formula VII or a tropinone of formula IX,

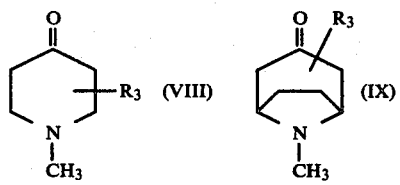

wherein $R_3$ is hydrogen or methyl, in the presence of an alkali metal hydride or an alkali metal alkoxide (e.g. potassium tert. butoxide) in a solvent at temperatures of from 20° C. to the boiling point of the reaction mixture. Suitable solvents are ethers, such as diethyl ether or diisopropyl ether, but preferably tetrahydrofuran. Generally, mixtures are formed, e.g. when tropinone is used, in addition to a compound of formula I wherein R represents the (8-methyl-8-azabicyclo[3,2,1]oct-3-ylidene) methyl group, a compound of formula I is also obtained wherein R is (2,3-dehydro-8-methyl-8-azabicyclo[3,2,-1]oct-3-yl)methyl group. Mixtures of this kind can usually be separated into their individual components quite easily, e.g. by column chromatography.

(d) In order to prepare compounds of formula I wherein R is (1-methyl-4-piperidinyl)methyl or an endo or exo-(8-methyl-azabicyclo[3,2,1]oct-3-yl)methyl group, optionally substituted by one or two further methyl groups in the heterocyclic six-membered ring, a dibenzodiazepinone of formula X

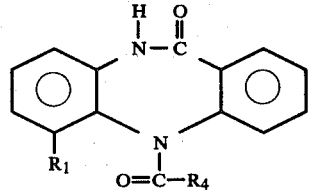

wherein $R_1$ is as hereinbefore defined and $R_4$ is

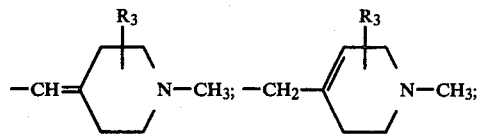

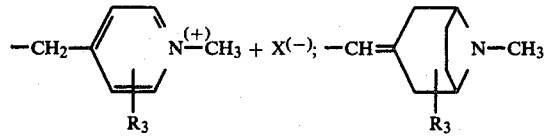

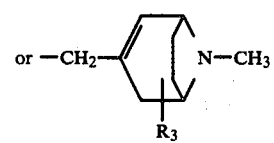

($R_3$ in these groups is hydrogen or methyl and X is halogen, preferably chlorine or bromine) may also be catalytically hydrogenated. Hydrogenation may, for example, be carried out with platinum dioxide as the catalyst at a pressure of between 1 and 50 bars, advantageously at 2 to 10 bars and at a temperatures of between −20° and +100° C., advantageously at ambient temperature. Instead of platinum dioxide, it is also possible to use finely divided palladium on charcoal, Raney nickel or Raney cobalt. The product to be hydrogenated is generally dissolved beforehand, e.g. in an alcohol such as ethanol.

(e) All the compounds of formula I, however, may be prepared from a dibenzodiazepinone of formula II

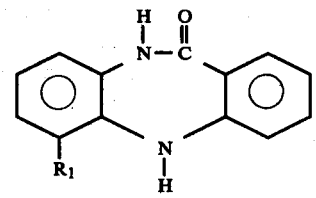

wherein $R_1$ is as hereinbefore defined, by first converting this compound into its dilithium salt with a lithium alkyl or lithium aryl and then reacting this dilithium salt with an ester of formula XII

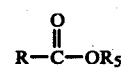

wherein R is as hereinbefore defined and $R_5$ represents an alkyl group with 1 to 10 carbon atoms, preferably 1 to 6 carbon atoms, or an aralkyl group with 7 to 13 carbon atoms, for example the phenylmethyl, phenylethyl or phenylpropyl group.

The conversion of the dibenzodiazepinone into its dilithium salt may be effected, in particular, with n-butyllithium, n-butyllithium in the presence of tetramethyl ethylenediamine, tert. butyllithium lithium diisoporopylamide, lithium dicyclohexylamide or with lithium aryls such as lithium phenyl. The conversion into the lithium salt and the further reaction with a compound of formula XII are effected in an organic solvent at temperatures of between −60° C. and 0° C., but preferably at about 10° C. The organic solvents used are those conventionally used for reactions with lithium alkyls or aryls; it is particularly advantageous to use tetrahydrofuran or ethers such as diethyl ether, aliphatic hydrocarbons such as hexane, or mixtures thereof, optionally also in the presence of hexamethyl phosphoramide as a cosolvent. Shortly after the addition of the lithium alkyl or aryl, a stoichiometric quantity or a slight excess of the ester of formula XII is added and the reaction mixture allowed to return slowly to ambient temperature, e.g. within 2 hours. The reaction product is isolated using known methods.

Some of the dibenzodiazepinones of formula I of the invention contain one or two asymmetric carbon atoms in the group R. These compounds may therefore occur in two diastereomeric cis and trans forms or as the enantiomeric (+) and (−) forms. The invention includes the individual isomers and the mixtures thereof.

The diastereomers may be separated on the basis of their different physico-chemical properties, e.g. by fractional recrystallization from suitable solvents or by chromatographic methods. Only one diastereomer is obtained if the method of synthesis (a) described above is carried out with only one diastereomer of formula III.

Any racemates of the compounds of formula I may be separated according to known methods, for example using an optically active acid such as (+)- or (−)-tartaric acid or a derivative thereof, such as (+)- or (−)-diacetyl tartaric acid, (+)- or (−)-monomethyl tartrate or (+)-camphorsulfonic acid.

In a conventional method for separating isomers, the racemate of a compound of formula I is reacted with an equimolar quantity of one of the above mentioned optically active acids in a solvent and the crystalline optically active salts obtained are separated on the basis of their different solubilities. This reaction may be carried out in any type of solvent provided that the salts have sufficiently different solubilities therein. Preferably, methanol, ethanol or a mixture thereof, for example in proportions of 50:50 by volume, is used. Then each of the optically active salts is dissolved in water and neutralized and in this way the corresponding free compound is obtained in the (+) or (−) form.

Only one enantiomer is obtained when the method of synthesis (a) described above is carried out with only one enantiomer of formula III.

The 5,10-dihydro-11H-dibenzo[b,e][1,4]diazepin-11-ones of formula II required as starting materials are known from the literature (e.g. F. Hunziker et al., Arzneim. Forsch. 13, 324 [1963]).

Compounds of formula III and IV are known or may readily be obtained analogously to known methods of preparation. For example, by reacting the sodium salt of 4-hydroxy-1-methyl-4-piperidino-acetic acid with thionyl chloride, a mixture of 1-methyl-1,2,5,6-tetrahydro-4-pyridinoacetic acid chloride and (1-methyl-4-piperidinylidene)acetyl chloride is obtained, which can be reacted according to process (a), without being separated, with a dibenzodiazepinone of formula II to form a mixture of the desired compounds of formula I, wherein R is (1-methyl-1,2,5,6-tetrahydro-4-pyridinyl)-methyl and (1-methyl-4-piperidinylidene)methyl group. If desired, this mixture of double bond isomers can subsequently be separated into its components by the usual methods, for example fractional crystallization, column chromatography or high pressure liquid chromatography.

Moreover, tropane-3α-acetic acid and tropane-3β-acetic acid can each be obtained, free from the other isomers, using the method described by W. Schneider et al., Arch. Pharm. 308, 365–375 (1975) and Ch. L. Zirke et al., J. Org. Chem. 27, 1279–1285 (1962). The reactive acid derivatives of these compounds may be the acid chlorides, which can be prepared in the usual way from the carboxylic acids mentioned above by converting them into the potassium salt and subsequently treating them with purified thionyl chloride.

Optionally methyl- or dimethyl-substituted 4-pyridinoacetic acids or isonicotinic acids are commercially available or may be synthesized analogously to or by means of an Arndt-Eistert reaction via the substituted isonicotinic acids described by D. Jerchel et al., Liebigs Ann. Chem. 613, 153–170 (1958) or by R. Likes et al., Collect. Czechoslov. Chem. Commun. 23, 1083–1089 (1958); 27, 2220–2222 (1962). The reactive acid derivatives used may be, for example, the acid chloride hydrochlorides, which may be obtained according to or analogously to the method described by H. Leditschke, Arch. Pharm. 295, 328 (1962).

As already mentioned hereinbefore, the new compounds of general formula I have valuable pharmacological properties; in particular, they have antiulcerogenic effects and they inhibit gastric acid secretion and they have favourable effects on various other disorders of the gastrointestinal tract, including, in particular, irritable colon.

A favourable balance between antiulcerogenic and antisecretory effects, on the one hand, and the undesirable effects on pupil size and the secretion of tears and saliva, on the other hand, which occur particularly with therapeutic agents having an anticholinergic component, is of particular importance in the therapeutic use of the substances. The following tests show that the compounds according to the invention having surprisingly favourable characteristics in this respect.

INVESTIGATION OF THE SELECTIVITY OF THE ANTIMUSCARINIC ACTIVITY

Aims

Oxotremorine, a specific agonist for muscarinic receptors, produces lesions in the mucous membrane of the stomach in rats and increases their secretion of saliva. This test method was chosen so that any selective activity of an antimuscarinic substance on the stomach could be identified.

Method 10 female albino rats (of the Crl:COBS-CD (SD) BR strain) with a body weight of from 120 to 150 g were used in each treatment group and were kept without food for 24 hours before the start of the test but given free access to drinking water.

In order to determine, in preliminary tests, the muscarinic effect of oxotremorine on each of the symptoms studied, a dosage/activity curve was drawn up with at least three dosages for each symptom.

When testing the antimuscarinic substances, the dosage of oxotremorine which triggered the symptom in question in 90 to 100% of the animals in the preliminary tests was used.

Lesions in mucous membrane of stomach: 0.62 mg/kg i.v.

Secretion of saliva: 0.083 mg/kg i.v.

Each antimuscarinic substance was administered intravenously in uniformly graduated doses 15 minutes before the oxotremorine was administered. Control groups were given corresponding quantities of the solvent and suspending agent instead of the test substance.

Immediately after the oxotremorine was administered, the animals were placed in a glass case for 15 minutes and observed.

The test for the effect on the oxotremerine-induced secretion of saliva was carried out as a double blind test, i.e. the tester did not know which treatment the animals had been given.

The results were expressed as the percentage inhibition of the oxotremorine effect (the percentage of animals which did not show the sympton in question). The $ED_{50}$ values were determined using the method described by LITCHFIELD and WILCOXON (J. Pharmacol. Exp. Ther. 96, 99, 1949).

The effects on lesions of the mucous membrane of the stomach were evaluated as follows:

The lesions of the gastric mucous membrane were produced by intravenous injection of 0.62 mg/kg of oxotremorine 30 minutes after the oral administration of 1 mg/kg of neostigmine (a cholinesterase inhibitor). 60 minutes after the administration of the neostigmine, the animals were killed, the stomachs were removed and opened and examined for the presence of any lesions in the mucous membrane. The protective effect of the test substances was expressed as the percentage inhibition (percentage of animals without lesions). The $ED_{50}$ and $ED_{70}$ values were determined using the method of LITCHFIELD and WILCOXON (see above).

MYDRIASIS

The effect of the test substances on the pupil size in rats was investigated as follows:

The substances were administered intravenously to groups of 10 animals in at least three uniformly graduated doses. The pupil size was then observed for 10 minutes to see if there were any changes (mydriasis or miosis) and again the test was carried out double blind, i.e. the tester did not know what preliminary treatment the animals had received. The percentage of test animals in which mydriasis occurred was determined. The $ED_{50}$ values were again determined using the method of LITCHFIELD and WILCOXON (see above).

2. Studies of binding to muscarinic receptors: Determination of the $IC_{50}$ value The organ donors were male Sprague-Dawley rats with a body weight of from 180 to 220 g. After the heart, stomach and cerebral cortex had been removed, the remainder of the operation was carried out in ice-cold Hepes-HCl buffer (pH 7.4; 100 m molar NaCl, 10 m molar $MgCl_2$). The smooth muscle of the fundus of the stomach was separated from the mucous membrane of the stomach and subjected to preliminary homogenization. The whole heart was cut up with scissors. All the organs were then homogenized in a Potter apparatus.

For the binding test, the homogenized organs were diluted as follows:
Smooth muscle of the fundus of the stomach: 1:100
Whole heart: 1:250
Cerebral cortex: 1:3000

The homogenized organ preparations were incubated at a specific concentration of the radiolabelled compound and with a series of concentrations of the non-radioactive test substances in an Eppendorf centrifuge tube at 30° C. The duration of incubation was 45 minutes. 0.3 n molar $^3$H-N-methylscopolamine ($^3$H-NMS) was used as the radiolabelled compound. After incubation had been brought to an end by centrifuging at 14000 g, the radioactivity in the pellet was determined. It represents the sum of the specific and nonspecific binding of $^3$H-NMS. The proportion of nonspecific binding was defined as the radioactivity which was bound in the presence of $1\mu$ molar quinuclidinylbenzylate. Four measurements were taken in each case. The $IC_{50}$ values of the non-labelled test substances were determined graphically. They represent the concentration of test substance at which the specific binding of $^3$H-NMS to the muscarinic receptors in the various organs was inhibited by 50%.

The following compounds were tested, for example, by the method described above:

A=5,10-dihydro-5-[(1-methyl-1,2,5,6-tetrahydro-4-pyridinyl)-carbonyl]-11H-dibenzo[b,e][1,4]diazepin-11-one B=6-chloro-5,10-dihydro-5-[(1-methyl-4-piperidinyl)acetyl]-11H-dibenzo[b,e][1,4]diazepin-11-one C=endo-5,10-dihydro-5-[(8-methyl-8-azabicyclo[3,2,1]-oct-3-yl)acetyl]-11H-dibenzo[b,e][1,4-]diazepin-11-one

| | Results: | | | | | | |
|---|---|---|---|---|---|---|---|
| | Receptor binding tests $IC_{50}$ [n mol $l^{-1}$] | | | Oxotremorine Test [μg/kg] i.v. | | | Mydriasis $ED_{50}$ i.v. [μg/kg] |
| | | | | Antiulcerative effect | | Inhibition of salivation | |
| Substance | Cortex | Smooth muscle fundus of stomach | Heart | $ED_{50}$ | $ED_{70}$ | $ED_{50}$ | |
| A | 30 | 100 | 250 | 3.1 | 6.5 | 80 | 36.6 |
| B | 28 | 170 | 200 | 4.4 | 8.4 | 230 | 138 |
| C | 15 | 200 | 55 | 1.1 | 3.8 | 105 | 54 |

The results in the above table show that the compounds mentioned generally have a high affinity with muscarinic receptors. Moreover, the results show that the new compounds of formula I differentiate between muscarinic receptors in different types of tissue. This is clear from the considerably lower $IC_{50}$ values in the tests on preparations from the cerebral cortex compared with those of the smooth muscle of the stomach and heart.

The pharmacological data in the above table show, in complete agreement with the receptor binding studies, that the formation of oxotremorine-induced lesions in the mucous membrane of the stomach is inhibited by the above mentioned compounds even at doses at which no restriction of salivation and no mydriasis can be observed.

The following Examples serve to illustrate the invention. "M.p." indicates "melting point", "D." indicates "decomposition".

EXAMPLES

Example 1

5,10-dihydro-5-[(1-methyl-1,2,5,6-tetrahydro-4-pyridinyl)acetyl]-11H-dibenzo[b,e][1,4]diazepin-11-one 5.8 ml (0.081 mol) of thionyl chloride, dissolved in 20 ml of chloroform, were added dropwise to a suspension of 14.0 g (0.072 mol) of the potassium salt of 1-methyl-1,2,5,6-tetrahydro-4-pyridinoacetic acid in 150 ml of anhydrous chloroform, with external cooling and with the reaction temperature being maintained at +15° C. The mixture was stirred for a further 20 minutes and then concentrated to dryness in vacuo. The residue remaining was added to a suspension of 8.4 g (0.04 mol) of 5,10-dihydro-11H-dibenzo[b,e][1,4]-diazepin-11-one in a mixture of solvents consisting of 300 ml of absolute dioxan and 20 ml of anhydrous pyridine. The mixture was heated to 80° C. for 2 hours with vigorous stirring. After cooling, it was filtered and the filter residue was taken up in water. It was then made alkaline with solid sodium carbonate and the aqueous phase was extracted exhaustively with chloroform. The combined chloroform extracts were dried and the solvent was removed in vacuo. The residue was purified by column chromatography on silica gel using ethyl acetate/methanol (ratio of volumes 9:1) as eluent. The substance isolated was an amorphous product. Yield: 3.5 g (25% of theory).

$C_{21}H_{21}H_3O_2$ (347.42). Calculated: C 72.6, H 6.09, N 12.09. Found: C 71.9, H 6.31, N 12.14.

IR (KBr): C=O 1669, shoulder 1680 cm$^{-1}$.

UV (ethanol): shoulder at $\lambda=270$ nm. (ethanol/KOH): $\lambda_{max}$ 290 nm (E=0.08), shoulder at $\lambda=260$ nm (E=0.105).

$^1$H-NMR (d$_6$-DMSO, 80 MH): $\delta=7.1$–7.9 (8H-m, aromat.H); 5.02 broad, 1H, olef.H); 2.95 broad (2H, C=C—CH$_2$N) 2.68 (2H, N—CH$_2$); 2.15 to 2.5 (2H-m; CO—CH$_2$); 2.18 (3H-s; NCH$_3$); 1.84 broad (2H; c=c—CH$_2$), 12.00 broad (1H-s; exchangeable H).

Example 2

5,10-dihydro-5-[(1-methyl-1,2,5,6-tetrahydro-4-pyridinyl)acetyl]-11H-dibenzo[b,e][1,4]diazepin-11-one
and
5,10-dihydro-5-[(1-methyl-4-piperidinylidene)acetyl]-11H-dibenzo[b,e][1,4]diazepin-11-one A solution of 14.2 g (0.12 mol) of thionyl chloride in 50 ml of chloroform was added dropwise to a suspension of 16.8 g (0.08 mol) of the potassium salt of 4-hydroxy-1-methyl-4-piperidinoacetic acid in 300 ml of chloroform, with external cooling and with the reaction temperature being maintained at 15° C. After being stirred for 20 minutes, the mixture was concentrated by evaporation in vacuo, and the residue was purified by column chromatography on aluminium oxide (activity stage 1) using ethyl acetate/methyanol (volume ratio 99:1) as eluent. 2.5 g (18% of theory) of 5,10-dihydro-5-[(1-methyl-1,2,5,6-tetrahydro-4-pyridinyl)acetyl]-11H-dibenzo[b,e][1,4]diazepin-11-one were obtained (absolutely identical, according to thin layer chromatogram, IR and NMR spectra, to a product prepared according to Example 1), and 0.2 g (1,4% of theory) of 5,10-dihydro-5-[(1-methyl-4-piperidinylidene)acetyl]-11H-dibenzo[b,e][1,4]diazepin-11-one was obtained, m.p. 200°–201° C.

The following were obtained analogously:

6-chloro-5,10-dihydro-5-[(1-methyl-1,2,5,6-tetrahydro-4-pyridinyl)-acetyl]-11H-dibenzo[b,e][1,4]diazepin-11-one
and
6-chloro-5,10-dihydro-5-[(1-methyl-4-piperidinylidene)acetyl]-11H-dibenzo[b,e][1,4]diazepin-11-one By reacting 4-hydroxy-1-methyl-4-piperidinoacetic acid and 6-chloro-5,10-dihydro-11H-dibenzo[b,e][1,4]-diazepin-11-one in a yield of 31% of theory. The 6-chloro-5,10-dihydro-5-[(1-methyl-1,2,5,6-tetrahydro-4-pyridinyl)-acetyl]-11H-dibenzo[b,e][1,4]diazepin-11-one was obtained as an amorphous powder with a decomposition point of 180° C.;

$C_{21}H_{20}ClN_3O_2$ (381.87). Calculated: C 66.05, H 5.28, Cl 9.28, N 11.01. Found: C 66.12, H 5.07, Cl 9.00, N 11.20.

$^1$N-NMR(CDCl$_3$, 80 MHz): $\delta=7.9$ (1H-m; aromat. H in the 1-position); 6.9–7.6 (6H-m; aromat. H); 4.9 and 5.15 (1H, olef. H); 2.8–3.05 (4H-m; 2CH$_2$); 2.4–2.65 (2H-m, CH$_2$); 2.3 and 2.35 (3H, N—CH$_3$); 2.05 (2H, CH$_2$);

6-Chloro-5,10-dihydro-5-[(1-methyl-4-piperidinylidene)-acetyl]-11H-dibenzo[b,e][1,4]diazepin-11-one was also obtained, in a yield of 10%, as an amorphous powder with a decomposition point of 155° C.

$C_{21}H_{20}ClN_3O_2$ (381.87). Calculated: 66.05, H 5.28, Cl 9.28, N 11.01. Found: C 66.15, H 5.32, Cl 9.09, N 11.03.

$^1$H-NMR(CDCl$_3$): $\delta=7.9$–8.1 (1H-m; aromat. H in the 1-position); 6.9–7.65 (6H-m, aromat. H); 5.4 and 5.55 (1H, olef. H); 2.8–3.05 (2H-m, CH$_2$); 1.95–2.55 (6H-m; 3CH$_2$); 2.2 (3H,N—CH$_3$).

EXAMPLE 3 endo-5,10-Dihydro-5-[(8-methyl-8-azabicyclo(3,2,-1)oct-3-yl)-acetyl]-11H-dibenzo[b,e][1,4]diazepin-11-one Prepared analogously to Example 2 from the potassium salt of tropane-3α-acetic acid and 5,10-dihydro-11H-dibenzo[b,e][1,4]diazepin-11-one in a yield of 33% of theory.

M.p. 226°–227° C. (ethyl acetate).

The following was obtained analogously:
Endo-6-Chloro-5,10-dihydro-5-[(8-methyl-8-azabicyclo(3,2,1)oct-3-yl)-acetyl]-11H-dibenzo[b,e][1,4-]diazepin-11-one By reacting the potassium salt of tropan-3α-acetic acid and 6-chloro-5,10-dihydro-11H-dibenzo[b,e][1,4]-diazepin-11-one in a yield of 27% of theory as an amorphous powder;

$C_{23}H_{24}ClN_3O_2$ (409.93). Calculated: C 67.39, H 5.90, Cl 8.65, N 10.25. Found: C 67.42, H 5.85, Cl 8.60, N 10.08.

$^1$H-NMR(CDCl$_3$): $\delta=7.8$–8.0 (1H-m; aromat. H in the 1-position); 7.0–7.6 (6H-m; aromat. H); 1.3–3.2 (16H-m, CH, CH$_2$ and N—CH$_3$ at 2.2).

IR (KBr): C=O 1665, shoulder 1675 cm$^{-1}$.

Example 4

5,10-Dihydro-5-[(1-methyl-4-piperidinyl)acetyl]-11H-dibenzo[b,e][1,4]diazepin-11-one Prepared analogously to Example 2 from the potassium salt of 1-methyl-4-piperidinoacetic acid and 5,10-dihydro-11H-dibenzo[b,e][1,4]diazepin-11-one in a yield of 26% of theory. Waxy substance, m.p. >95° C.

$C_{21}H_{23}N_3O_2$ (349.43). Calculated: C 72.18, H 6.63, N 12.03. Found: C 71.72, H 7.07, N 14.90.

MS: (m/e)=349 (201; 140; 96)

IR (CH$_2$Cl$_2$): NH 3375, CO 1660 and 1676 cm$^{-1}$

UV (ethanol): shoulder at λ270 nm

UV (ethanol/KOH): $\lambda_{max}$290 nm (E=0.095); shoulder at λ256 nm (E=0.12)

$^1$H-NMR (CDCl$_3$/D$_2$O; 80 MHz): δ=7.7–8.0 (1H-m; aromat. H); 7.0–7.6 (7H-m; ar.H); 2.5–2.9 (2H-m); 0.8–2.4 (12H-m), then at δ=2.12 (3H-s; N—CH$_3$)

The following were obtained analogously:

5,10-dihydro-5-[(1,3-dimethyl-4-piperidinyl)acetyl]-11H-bibenzo[b,e][1,4]diazepin-11-one From 5,10-dihydro-11H-dibenzo[b,e][1,4]diazepin-11-one and the potassium salt of 1,3-dimethyl-4-piperidinoacetic acid in a yield of 45% of theory, m.p. 175° C.; MS: (m/e)=363;

5,10-dihydro-5-[(1,2-dimethyl-4-piperidinyl)acetyl]-11H-dibenzo[b,e][1,4]diazepin-11-one From 5,10-dihydro-11H-dibenzo[b,e][1,4]diazepin-11-one and the potassium salt of 1,2-dimethyl-4-piperidinoacetic acid in a yield of 38% of theory; MS: (m/e)=363;

IR(KBr): C=O 1665 cm$^{-1}$.

exo-5,10-dihydro-5-[(8-methyl-8-azabicyclo[3,2,1]oct-3-yl)acetyl]-11H-dibenzo[b,e][1,4]diazepin-11-one From 5,10-dihydro-11H-dibenzo[b,e][1,4]diazepin-11-one and the potassium salt of tropan-3β-acetic acid in a yield of 48% of theory, m.p. 148°–150° C.; and exo-6-chloro-5,10-dihydro-5-[(8-methyl-8-azabicyclo[3,2,1]oct-3-yl)-acetyl]-11H-dibenzo[b,e][1,4-]diazepin-11-one From 6-chloro-5,10-dihydro-11H-dibenzo[b,e][1,-4diazepin-11-one and the potassium salt of tropan-3β-acetic acid in a yield of 51% of theory;

$C_{23}H_{24}ClN_3O_2$ (409.93). Calculated: C 67.39, H 5.90, Cl 8.65, N 10.25. Found: C 67.30, H 5.82, Cl 8.91, N 10.09.

IR(KBr): C=O 1665 cm$^{-1}$

Example 5

6-chloro-5,10-dihydro-5-[(1-methyl-4-piperidinyl)acetyl]-11H-dibenzo[b,e][1,4]diazepin-11-one A mixture of 1.7 g (21 mmol) of pyridine and 30 ml of dioxan was added dropwise at ambient temperature within 20 minutes to a suspension of 1.8 g (7 mmol) of 6-chloro-5,10-dihydro-11H-dibenzo[b,e][1,4]diazepin-11-one and 7.0 g (28 mmol) of 1-methyl-4-piperidinoacetic acid chloride hydrochloride in 200 ml of dioxan. The mixture was stirred at ambient temperature for 7 hours and then the reaction mixture was filtered. The solid portions were distributed between chloroform and an aqueous potassium carbonate solution. The organic phase was dried over magnesium sulphate, treated with animal charcoal, filtered and concentrated by evaporation. The residue was purified by column chromatography on silica gel (Macherey & Nagel MN 60; eluent; chloroform/ethyl acetate/methanol in a ratio by volume of 1:1:1) and after trituration with cyclohexane 0.85 g (32% of theory) of 6-chloro-5,10-dihydro-5-[(1-methyl-4-piperidinyl)acetyl]-11H-dibenzo-[b,e][1,4]diazepin-11-one was obtained.

$C_{21}H_{22}ClN_3O_2$ (383.88). Calculated: C 65.71, H 5.78, Cl 9.24, N 10.95. Found: C 65.90, H 6.02, Cl 8.78, N 10.90.

$^1$H-NMR (CDCl$_3$; 80 MHz): δ=7.8–8.0 (1H-m; lar.H in the 1 position); 7.0–7.6 (6H-m; ar.H); 2.2 (3H-s; N—CH$_3$); 2.6–2.9 and 1.1–2.3 (11H-m,; aliph. H).

IR(CH$_2$Cl$_2$): NR 3400 and 3200 cm$^{-1}$; C=O 1670 and shoulder 1690 cm$^{-1}$ UV (ethanol): λ=270 nm; (ethanol/KOH): λ=259 nm and 289 nm.

6-chloro-5,10-dihydro-5-[(1-methyl-4-piperidinyl)acetyl]-11H-dibenzo[b,e][1,4]diazepin-11-one is crystallized from ethyl acetate with ½ mol of ethyl acetate: m.p. 147° C.

Example 6

5,10-dihydro-5-[(1-methyl-1,2,5,6-tetrahydro-4-pyridinyl)carbonyl]-11H-dibenzo[b,e][1,4]diazepin-11-one-hemihydrate A mixture of 10.65 g (0.051 mol) of 5,10-dihydro-11H-dibenzo[b,e][1,4]diazepin-11-one, 19.6 g (0.10 mol) of 1-methyl-1,2,5,6-tetrahydroisonicotinic acid chloride hydrochloride, 20.7 g (0.15 mol) of potassium carbonate and 200 ml of anhydrous toluene were refluxed for 24 hours, with thorough stirring. After cooling, the mixture was stirred into 500 ml of ice-cold water, the organic layer was separated off and the aqueous layer was exhaustively extracted with ethyl acetate. The combined organic phases were dried over sodium sulphate then concentrated by evaporation in vacuo. The residue was purified by column chromatography, first on silica gel with a particle size of 0.1 to 0.4 mm, using 1,2-dichloroethane/methanol as eluant (ratio by volume 9:1), and secondly on silica gel with a particle size of from 0.05 to 0.2 mm, using 1,2-dichloroethane/methanol (volume ratio 95:5) as eluant. When the appropriate fractions were worked up in the usual way, colorless crystals were obtained, m.p. 233°–234° C. (diisopropylether/ethyl acetate). Yield: 2.4 g (14% of theory).

Example 7

5,10-dihydro-5-[(1-methyl-1,2,5,6-tetrahydro-4-pyridinyl)carbonyl]-11H-dibenzo[b,e][1,4]diazepin-11-one-hemihydrate (a) 5,10-dihydro-5-[(4-pyridinyl)carbonyl]-11H-dibenzo[b,e][1,4]diazepin-11-one A mixture of 21.0 g (0.1 mol) of 5,10-dihydro-11H-dibenzo[b,e][1,4]diazepin-11-one, 23.0 g (0.129 mol) of isonicotinic acid chloride hydrochloride, 21 ml (0.26 mol) of pyridine and 300 ml of anhydrous dioxan was refluxed for 3 hours. After cooling, the mixture was poured into 1 liter of ice-cold water, acidified with conc. hydrochloric acid and extracted twice, each time with 200 ml of dichloromethane. The aqueous phase was made alkaline with methylene chloride. The combined methylene chloride extracts were washed with water, dried over sodium sulphate and the solvent was removed in vacuo. The residue was recrystallized from hot methanol. After washing with ether, the beige crystals melted at 277°–279° C. Yield 16.0 g (51% of theory).

(b) 5,10-dihydro-5-[(4-pyridinyl)carbonyl]-11H-dibenzo[b,e][1,4]diazepin-11-one methoiodide 6.3 g (0.02 mol) of 5,10-dihydro-5-[(4-pyridinyl)carbonyl]-11H-dibenzo[b,e][1,4]diazepin-11-one were dissolved in 100 ml od anhydrous dimethylformamide and, after the addition of 3.2 g (0.0227 mol) of iodomethane, the mixture was stirred overnight at ambient temperature. It was concentrated in vacuo down to one third of its original volume, then a mixture of equal parts by volume of methanol and ether was added until the salt formed began to crystallize out. After it had been left to stand for 2 hours at ambient temperature, it was suction filtered and the precipitate was washed thoroughgly with ether. 7.2 g (79% of theory) of yellow crystals were obtained, m.p. 297° C. (D).

(c) 5,10-dihydro-5-[(1-methyl-1,2,5,6-tetrahydro-4-pyridinyl)-carbonyl]-11H-dibenzo[b,e][1,4]-diazepin-11-one-hemihydrate 2.3 g (0.005 mol) of 5,10-dihydro-5-[(4-pyridinyl)carbonyl]-11H-dibenzo[b,e][1,4]diazepin-11-one methoiodide were suspended in 200 ml of methanol and at 0° C. 0.25 g (0.006 mol) of sodium borohydride were added in batches. The mixture was stirred for a further hour in the ice bath. It was then stirred into 1 liter of ice-cold water and extracted exhaustively with methylene chloride. The combined extracts were washed with water, dried over sodium sulphate and concentrated by evaporation in vacuo. After recrystallization from diisopropylether/methanol, the colorless crystals melted at 233°–234° C.

Yield: 0.9 g (53% of theory).

According to the thin layer chromatogram, IR and NMR spectra, the product was identical to a product prepared according to Example 6.

Example 8

5,10-dihydro-5-[(1,2,6-trimethyl-1,2,5,6-tetrahydro-4-pyridinyl)carbonyl)-11H-dibenzo[b,e][1,4]diazepin-11-one Prepared analogously to Example 7(a) from 5,10-dihydro-11H-dibenzo[b,e][1,4]diazepin-11-one and 2,6-dimethylisonicotinic acid chloride hydrochloride (m.p. 135°–138° C.) in a yield of 54% of theory. Light beige crystals, m.p. 273°–275° C. (methanol, using active charcoal).

(b) 5,10-dihydro-5-[(2,6-dimethyl-4-pyridinyl)carbonyl]-11H-dibenzo[b,e][1,4]diazepin-11-one methoiodide Prepared analogously to Example 7(b) from 5,10-dihydro-5-[(2,6-dimethyl-4-pyridinyl)carbonyl]-11H-dibenzo[b,e][1,4]diazepin-11-one and iodomethane in a yield of 62% of theory. The yellow crystals melted, with decomposition, at 298°–300° C.

(c) 5,10-dihydro-5-[(1,2,6-trimethyl-1,2,5,6-tetrahydro-4-pyridinyl)carbonyl]-11H-dibenzo[b,e][1,4]diazepin-11-one Prepared analogously to Example 7(c) from 5,10-dihydro-5-[(2,6-dimethyl-4-pyridinyl)carbonyl]-11H-dibenzo[b,e][1,4]diazepin-11-one methoiodide and sodium borohydride in methanol in a yield of 25% of theory. After purification by column chromatography on silica gel using dichloromethane/methanol (ratio by volume 9:1) as a eluent and recrystallizing from diisopropylether/methanol, the light beige crystals melted at 124°–125° C.

The following were obtained analogously:

5,10-dihydro-5-[(1,3-dimethyl-1,2,5,6-tetrahydro-4-pyridinyl)-carbonyl]-11H-dibenzo[b,e][1,4]diazepin-11-one
and
5,10-dihydro-5-[(1,5-dimethyl-1,2,5,6-tetrahydro-4-pyridinyl)-carbonyl]-11H-dibenzo[b,e][1,4]diazepin-11-one By reacting 5,10-dihydro-11H-dibenzo[b,e][1,4]diazepin-11-one with 3-methylisonicotinic acid chloride (m.p. 155°–156° C.) via 5,10-dihydro-5-[3-methyl-4-pyridinyl)carbonyl]-11H-dibenzo[b,e][1,4]diazepin-11-one, m.p. 223°–224° C. (diisopropylether/methanol) and 5,10-dihydro-5[(3-methyl-4-pyridinyl)carbonyl]-11H-dibenzo[b,e][1,4]-diazepin-11-one methoiodide;

5,10-dihydro-5-[(1,2-dimethyl-1,2,5,6-tetrahydro-4-pyridinyl)-carbonyl]-11H-dibenze[b,e][1,4]diazepin-11-one
and
5,10-dihydro-5-[(1,6-dimethyl-1,2,5,6-tetrahydro-4-pyridinyl)-carbonyl]-11H-dibenzo[b,e][1,4]diazepin-11-one;

From 5,10-dihydro-11H-dibenzo[b,e][1,4]diazepin-11-one and 2-methylisonicotinic acid chloride hydrochloride via 5,10-dihydro-5-[(2-methyl-4-pyridinyl)carbonyl]-11H-dibenzo[b,e][1,4]diazepin-11-one and 5,10-dihydro-5-[(2-methyl-4-pyridinyl)carbonyl]-11H-dibenzo[b,e][1,4]diazepin-11-one methoiodide.

6-chloro-5,10-dihydro-5-[(1-methyl-1,2,5,6-tetrahydro-4-pyridinyl)carbonyl]-11H-dibenzo[b,e][1,4]diazepin-11-one from 6-chloro-5,10-dihydro-11H-dibenzo[b,e][1,4]diazepin-11-one and isonicotinic acid chloride hydrochloride via 6-chloro-5,10-dihydro-5-[(4-pyridinyl)carbonyl]-11H-dibenzo[b,e][1,4]diazepin-11-one and 6-chloro-5,10-dihydro-5-[(4-pyridinyl)carbonyl]-11H-dibenzo[b,e][1,4]diazepin-11-one methoiodide; m.p. 296° C. (from methanol) in a total yield of 53% of theory, obtained as an amorphous substance by treating with methanol and diisopropylether;

IR spectrum ($CH_2Cl_2$): NH 3380 $cm^{-1}$; C=O 1675 $cm^{-1}$, 5,10-dihydro-5-[(1-methyl-1,2,5,6-tetrahydro-4-pyridinyl)acetyl]-11H-dibenzo[b,e][1,4]diazepin-11-one from 5,10-dihydro-11H-dibenzo[b,e][1,4]diazepin-11-one and 4-pyridioacetic acid chloride hydrochloride via 5,10-dihydro-5-[(4-pyridinyl)acetyl]-11H-dibenzo[b,e]-[1,4]diazepin-11-one and 5,10-dihydro-5-[(4-pyridinyl)acetyl]-11H-dibenzo[b,e][1,4]diazepin-11-one methoiodide.

Example 9

5,10-dihydro-5-[(1-methyl-1,2,5,6-tetrahydro-4-pyridinyl)acetyl]-11H-dibenzo[b,e][1,4]diazepin-11-one A mixture of 0.97 g (6.25 mol) of 1-methyl-1,2,5,6-tetrahydro-4-pyridinoacetic acid and 0.20 g (6.25 mmol) of 75% sodium hydride (in paraffin oil) in 16 ml of dimethylformamide was heated to 50°–80° C. until the development of hydrogen had ceased (2 to 3 hours). 1.312 g (6.24 mmol) of 5,10-dihydro-11H-dibenzo[b,e][1,4]-diazepin-11-one was added to the sodium salt of the acid thus produced and at −10° C. 0.99 g of 98% phosphorus oxytrichloride was added dropwise within 10 minutes. The resulting mixture was stirred at −10° C. for 4 hours, at 0° C. for 4 hours and at ambient temperature for 20 hours. The mixture was stirred into 200 g of crushed ice, adjusted to pH 3.5 with sodium hydroxide solution, extracted once with methylene chloride and then the aqueous phase was adjusted to pH 9 and exhaustively extracted with methylene chloride. The organic phase was washed with water, dried over sodium sulphate and concentrated by evaporation in vacuo. After purification by column chromatography on silica gel (using ethyl acetate/methanol in a volume ratio of 9:1 as eluent) 0.63 g (29% of theory) of a colorless amorphous product was obtained, which was identical, according to the thin layer chromatogram, elementary analysis and IR spectrum, to a compound obtained using the method of Example 1.

The following were obtained analogously:

Endo-5,10-dihydro-5-[(8-methyl-8-azabicyclo[3,2,1]oct-3-yl)-acetyl]-11H-dibenzo[b,e][1,4]diazepin-11-one Exo-5,10-dihydro-5-[(8-methyl-8-azabicyclo[3,2,1]oct-3-yl)-acetyl]-11H-dibenzo[b,e][1,4]diazepin-11-one 5,10-dihydro-5[(1-methyl-4-piperidinyl)acetyl]-11H-dibenzo[b,e][1,4]diazepin-11-one 6-chloro-5,10-dihydro-5-[(1-methyl-4-piperidinyl)acetyl]-11H-dibenzo[b,e][1,4]diazepin-11-one 5,10-dihydro-5-[(1-methyl-1,2,5,6-tetrahydro-4-pyridinyl)carbonyl]-11H-dibenzo[b,e][1,4]diazepin-11-one hemihydrate

Example 10

5,10-dihydro-5-[(1-methyl-1,2,5,6-tetrahydro-4-pyridinyl)acetyl]-11H-dibenzo[b,e][1,4]diazepin-11-one 1.1 g (10.14 mmol) of ethyl chlorocarbonate was added dropwise, at 0° C., to a suspension of 1.552 g (10 mmol) of 1-methyl-1,2,5,6-tetrahydro-4-pyridinoacetic acid in 20 ml of anhydrous tetrahydrofuran. 2.10 g (10 mmol) of 5,10-dihydro-11H-dibenzo[b,e][1,4]diazepin-11-one was added to the resulting mixture, which was then stirred for 1 hour at 0° C. and then for 4 hours at ambient temperature. The mixture was then stirred into 160 ml of 2 N sodium hydroxide solution, while external cooling with ice was carried out, and extracted exhaustively with dichloromethane. The organic phase was evaporated to dryness in vacuo. After purification by column chromatography on silica gel using ethyl acetate/methanol in a volume ratio of 9:1 as the eluent, 0.87 g (25% of theory) of a colorless, amorphous product was obtained, which was shown by thin layer chromatography and IR and NMR spectra to be identical to a compound synthesized using the method of Example 1.

Analogously:

From 5,10-dihydro-11H-dibenzo[b,e][1,4]diazepin-11-one and 1-methyl-1,2,5,6-tetrahydro-isonicotinic acid, 5,10-dihydro-5-[(1-methyl-1,2,5,6-tetrahydro-4-pyridinyl)carbonyl]-11H-dibenzo[b,e][1,4]diazepin-11-one hemihydrate was obtained, m.p. 233°-234° C. (diisopropylether/ethyl acetate;

From 5,10-dihydro-11H-dibenzo[b,e][1,4]diazepin-11-one and tropan-3α-acetic acid, endo-5,10-dihydro-5-[(8-methyl-8-azabicyclo[3,2,1]oct-3-yl)-acetyl]-11H-dibenzo[b,e][1,4]diazepin-11-one was obtained, m.p. 226°-227° C. (ethyl acetate);

From 5,10-dihydro-11H-dibenzo[b,e][1,4]diazepin-11-one and 1-methyl-4-piperidinoacetic acid, 5,10-dihydro-5-[(1-methyl-4-piperidinyl)acetyl]-11H-dibenzo[b,e][1,4]diazepin-11-one was obtained, which was identical, according to thin layer chromatography, IR and $^1$H-NMR spectra, to a compound obtained using the method of Example 4;

from 6-chloro-5,10-dihydro-11H-dibenzo[b,e][1,4]diazepin-11-one and 1-methyl-4-piperidinoacetic acid, 6-chloro-5,10-dihydro-5-[(1-methyl-4-piperidinyl)acetyl]-11H-dibenzo[b,e][1,4]diazepin-11-one was obtained, which was identical, according to thin layer chromatography and IR and NMR spectra, to a composition obtained using the method of Example 5.

Example 11

5,10-dihydro-5-[(8-methyl-2,3-dehydro-8-azabicyclo[3,2,1]-oct-3-yl)acetyl]-11H-dibenzo[b,e][1,4]diazepin-11-one and 5,10-dihydro-5-[(8-methyl-8-azabicyclo[3,2,1]oct-3-ylidene)acetyl]-11H-dibenzo[b,e][1,4]diazepin-11-one (a) 5-bromoacetyl-5,10-dihydro-11H-dibenzo[b,e][1,4]-diazepin-11-one 93 g (0.55 mol) of bromoacetyl chloride were added dropwise, with stirring, to a suspension of 105 g (0.5 mol) of 5,10-dihydro-11H-dibenzo[b,e][1,4]-diazepin-11-one in 1 liter of toluene, at 90° C. The mixture was then refluxed for a further 30 minutes, during which there was a strong development of hydrogen chloride. After cooling, the dark blue crystal slurry obtained was suction filtered;

m.p. 215°-216° C.;

Yield: 143 g (86% of theory)

(b) 5-diethylphosphono-acetyl-5,10-dihydro-11H-dibenzo[b,e][1,4]diazepin-11-one

A mixture of 143 g (0.43 mol) of 5-bromoacetyl-5,10-dihydro-11H-dibenzo[b,e][1,4]diazepin-11-one and 400 ml of triethylphosphite was refluxed for 2 hours at 120° C., with stirring. In the course of the reaction, the 5-bromoacetyl compound went fully into solution and a grey precipitate began to settle out. After cooling, this was suction filtered and washed with ethyl acetate and 159 g (95% of theory) of 5-diethylphosphonoacetyl-5,10-dihydro-11H-dibenzo[b,e][1,4]diazepin-11-one were obtained; m.p. 195°-197° C.

(c) 5,10-dihydro-5-[(8-methyl-2,3-dehydro-8-azabicyclo(3,2,1)oct-3-yl)-acetyl]-11H-dibenzo[b,e][1,4]diazepin-11-one and 5,10-dihydro-5-[(8-methyl-8-azabicyclo-(3,2,1)oct-3-ylidene)-acetyl]-11H-dibenzo[b,e][1,4]diazepin-11-one 15.9 g (0.041 mol) of 5-diethylphosphono-acetyl-5,10-dihydro-11H-dibenzo[b,e][1,4]diazepin-11-one were added in portions to a suspension of 3.92 g (0.082 mol) of sodium hydride (50%) in paraffin oil) in 160 ml of tetrahydrofuran at ambient temperature, with stirring. The solution of 5.7 g (0.041 mol) of tropinone in 10 ml of tetrahydrofuran was added dropwise to the reaction mixture and the resulting mixture was refluxed gently for 3 days. When the reaction had ended, the reaction solution was shaken with 100 ml of saturated sodium chloride solution. The resultant organic phase was diluted with 100 ml of ethyl acetate and extracted twice with 10% hydrochloric acid. The hydrochloric acid phase was made alkaline with solid potassium carbonate and extracted with ethyl acetate. The ethyl acetate solution was suction filtered over activated charcoal and, after drying, the residue was concentrated by evaporation in a rotary evaporator. The residue obtained was a brown oil which contained the two products as its main components. This oil was separated by column chromatography on silica gel (MN silica gel 60; 0.063-0.2 mm particle size; eluent: methylene chloride/methanol/ammonia=90:9:1). 5.1 g (33% of theory) of 5,10-dihydro-5-[(8-methyl-2,3-dehydro-8-aza-bicyclo(3,2,1)oct-3-yl)-acetyl]-11H-dibenzo[b,e][1,4]diazepin-11-one were obtained in the form of an amorphous powder;

$C_{23}H_{23}N_3O_2$ (373.44). Calculated: C 73.98, H 6.21, N 11.25. Found: C 74.12, H 6.18, N 11.20.

$R_f$ value: 0.3 (thin layer chromatography on silica gel, silical gel 60 $F_{254}$, layer thickness 0.25 mm; eluent: methylene chloride/methanol/cyclohexane/ammonia=68:15:15:2); and 4.3 g (28% of theory) of 5,10-dihydro-5-[(8-methyl-8-azabicyclo-(3,2.1)-oct-3-ylidene)-acetyl]-11H-dibenzo[b,e][1,4]diazepin-11-one were obtained, $C_{23}H_{23}N_3O_2$ (373.44). Calculated: C 73.98, H 6.21, N 11.25. Found: C 73.90, H 6.25, N 11.21.

$R_f$ value: 0.25 (thin layer chromatography on silica gel, silica gel 60 $F_{254}$, layer thickness 0.25 mm; eluent: methylene chloride/methanol/cyclohexane/ammonia=68:15:15:2).

The following were obtained analogously:
6-chloro-5,10-dihydro-5-[(8-methyl-2,3-dehydro-8-azabicyclo-(3,2,1)-oct-3-yl)acetyl]-11H-dibenzo[b,e][1,4]-diazepin-11-one
and
6-chloro-5,10-dihydro-5-[(8-methyl-8-azabicyclo(3,2,1)-oct-3-ylidene)acetyl]-11H-dibenzo[b,e][1,4]diazepin-11-one
from 5-bromoacetyl-6-chloro-5,10-dihydro-11H-dibenzo[b,e][1,4]diazepin-11-one, by way of
6-chloro-5-diethylphosphono-acetyl-5,10-dihydro-11H-dibenzo[b,e][1,4]diazepin-11-one;
and
5,10-dihydro-5-[(1-methyl-1,2,5,6-tetrahydro-4-pyridinyl)acetyl]-11H-dibenzo[b,e][1,4]diazepin-11-one
from 5-diethylphosphono-acetyl-5,10-dihydro-11H-dibenzo-[b,e][1,4]diazepin-11-one and N-methyl-piperidin-4-one,
and
6-chloro-5,10-dihydro-5-[(1-methyl-1,2,5,6-tetrahydro-4-pyridinyl)-acetyl]-11H-dibenzo[b,e][1,4]diazepin-11-one
from 6-chloro-5-diethylphosphono-acetyl-5,10-dihydro-11H-dibenzo[b,e][1,4]diazepin-11-one and N-methyl-piperidine-4-one.

EXAMPLE 12

5,10-dihydro-5-[(1-methyl-4-piperidinyl)acetyl]-11H-dibenzo[b,e][1,4]diazepin-11-one 3.5 g (0.01 mol) of 5,10-dihydro-5-[(1-methyl-1,2,5,6-tetrahydro-4-pyridinyl)acetyl]-11H-dibenzo[b,e][1,4-]diazepin-11-one were dissolved in 100 ml of ethanol and hydrogenated in the presence of 0.5 g of platinum oxide at ambient temperature and under a pressure of 3 bar. After the uptake of hydrogen had ended, the catalyst was filtered out and the remaining mixture concentrated by evaporation in vacuo. The residue was purified by column chromatography (NM silica gel 60; 0.063-0.2 mm particle size; eluent; ethyl acetate/methanol=9:1) and 3.2 g (91% of theory) of 5,10-dihydro-5-[(1-methyl-4-piperidinyl)acetyl]-11H-dibenzo[b,e][1,4]diazepin-11-one was obtained, which was identical, according to thin layer chromatography, elementary analysis and IR spectrum, to the product obtained using the method of Example 4.

The following were prepared analogously:
6-chloro-5,10-dihydro-5-[(1-methyl-4-piperidinyl)acetyl]-11H-dibenzo[b,e][1,4]diazepin-11-one
from
6-chloro-5,10-dihydro-5-[(1-methyl-1,2,5,6-tetrahydro-4-pyridinyl)acetyl]-11H-dibenzo[b,e][1,4]diazepin-11-one;
5,10-dihydro-5-[(1-methyl-4-piperidinyl)acetyl]-11H-dibenzo[b,e][1,4]diazepin-11-one
from
5,10-dihydro-5-[(1-methyl-4-piperidinylidene)acetyl]-11H-dibenzo[b,e][1,4]diazepin-11-one;
6-chloro-5,10-dihydro-5-[(1-methyl-4-piperidinyl)acetyl]-11H-dibenzo[b,e][1,4]diazepin-11-one
from
6-chloro-5,10-dihydro-5-[(1-methyl-4-piperidinylidene)acetyl]-11H-dibenzo[b,e][1,4]diazepin-11-one;
endo-5,10-dihydro-5-[(8-methyl-8-azabicyclo(3,2,1)oct-3-yl)-acetyl]-11H-dibenzo[b,e][1,4]diazepin-11-one
and
exo-5,10-dihydro-5-[(8-methyl-8-azabicyclo(3,2,1)oct-3-yl)-acetyl]-11H-dibenzo[b,e][1,4]diazepin-11-one
from
5,10-dihydro-5-[(8-methyl-2,3-dehydro-8-azabicyclo(3,2,1)-oct-3-yl)acetyl]-11H-dibenzo[b,e][1,4-]diazepin-11-one;
endo-5,10-dihydro-5-[(8-methyl-8-azabicyclo(3,2,1)oct-3-yl)-acetyl]-11H-dibenzo[b,e][1,4]diazepin-11-one
and
exo-5,10-dihydro-5-[(8-methyl-8-azabicyclo(3,2,1)oct-3-yl)-acetyl]-11H-dibenzo[b,e][1,4]diazepin-11-one
from
5,10-dihydro-5-[(8-methyl-8-azabicyclo(3,2,1)oct-3-ylidene)-acetyl]-11H-dibenzo[b,e][1,4]diazepin-11-one;
endo-6-chloro-5,10-dihydro-5-[(8-methyl-8-azabicyclo(3,2,1)-oct-3-yl)-acetyl]-11H-dibenzo[b,e][1,4-]diazepin-11-one
and
exo-6-chloro-5,10-dihydro-5-[(8-methyl-8-azabicyclo(3,2,1)oct-3-yl)-acetyl]-11H-dibenzo[b,e][1,4-]diazepin-11-one
from
6-chloro-5,10-dihydro-5-[(8-, ethyl-2,3-dihydro-8-azabicyclo(3,2,1)-oct-3-yl)acetyl]-11H-dibenzo[b,e][1,4]-diazepin-11-one;
endo-6-chloro-5,10-dihydro-5-[(8-methyl-8-azabicyclo(3,2,1)oct-3-yl)-acetyl]-11H-dibenzo[b,e][1,4-]diazepin-11-one
and
exo-6-chloro-5,10-dihydro-5-[(8-methyl-8-azabicyclo(3,2,1)oct-3-yl)-acetyl]-11H-dibenzo[b,e][1,4-]diazepin-11-one
from
6-chloro-5,10-dihydro-5-[(8-methyl-8-aza-bicyclo(3,2,-1)oct-3-ylidene)acetyl]-11H-dibenzo[b,e][1,4]diazepin-11-one;
5,10-dihydro-5-[(1-methyl-4-piperidinyl)acetyl]-11H-dibenzo[b,e][1,4]diazepin-11-one
from
5,10-dihydro-5-[(4-pyridinyl)acetyl]-11H-dibenzo[b,e][1,4]diazepin-11-one methoiodide.

EXAMPLE 13

6-chloro-5,10-dihydro-5-[(1-methyl-4-piperidinyl)acetyl]-11H-dibenzo[b,e][1,4]diazepin-11-one 32 ml (0.05 mol) of n-butyl lithium (15% in hexane) were added dropwise, with stirring, to a suspension of 5 g (0.02 mol) of 6-chloro-5,10-dihydro-11H-dibenzo[b,e][1,4]diazepin-11-one in 150 ml of tetrahydrofuran, at 0° C. The resulting mixture was then stirred for 30 minutes at ambient temperature. Then 5.6 g (0.03 mol) of the ethyl 1-methylpiperidino-4-acetate, dissolved in 25 ml of tetrahydrofuran, were added dropwise, again at 0° C., with stirring, and the resulting mixture was stirred for 2 hours at ambient temperature. The reaction mixture was then concentrated to about one third of its volume in vacuo and mixed with ice/water. After acidification with dilute hydrochloric acid, the mixture was extracted three times with ethyl acetate and the aqueous phase made alkaline with solid potassium carbonate under cold conditions. It was again extracted exhaustively with ethyl acetate. The extracts were dried, filtered and concentrated by evaporation in vacuo. After column chromatography on silica gel, 1.7 g (22% of theory) of 6-chloro-5,10-dihydro-5-[(1-methyl-4-piperidinyl)acetyl]-11H-dibenzo[b,e][1,4]diazepin-11-one was obtained, which was identical in its physical properties to the product of Example 5.

PHARMACEUTICAL FORMS

The preparation of some pharmaceutical forms will now be described with reference to some Examples:

EXAMPLE I

Tablets containing 5 mg of 6-chloro-5,10-dihydro-5-[(1-methyl-4-piperidinyl)acetyl]-11H-dibenzo[b,e][1,4]-diazepin-11-one

| Composition: | |
|---|---|
| Tablet contains: | |
| Active substance | 5.0 mg |
| Lactose | 148.0 mg |
| Potato starch | 65.0 mg |
| Magnesium stearate | 2.0 mg |
| | 220.0 mg |

Method of preparation

A 10% mucilage is prepared from potato starch by heating. The active substance, lactose and remaining potato starch are mixed together and granulated with the mucilage through a screen with a mesh size of 1.5 mm. The granulate is dried at 45° C., passed through the screen again, mixed with magnesium stearate and compressed to form tablets.
Weight of tablets: 220 mg
Die diameter: 9 mg

EXAMPLE II

Coated tablets containing 5 mg of 6-chloro-5,10-dihydro-5-[(1-methyl-4-piperidinyl)acetyl]-11H-dibenzo[b,e][1,4]-diazepin-11-one The tablets prepared according to Example I are coated by a known method with a shell consisting essentially of sugar and talc. The finished coated tablets are polished with beeswax.
Weight of coated tablet: 300 mg

EXAMPLE III

Ampoules containing 1 mg of 6-chloro-5,10-dihydro-5-[(1-methyl-4-piperidinyl)acetyl]-11H-dibenzo[b,e][1,4]-diazepin-11-one hydrochloride

| Composition: | |
|---|---|
| 1 ampoule contains: | |
| Active substance | 1.0 mg |
| Sodium chloride | 8.0 mg |
| Distilled water qs | 1 ml |

Method of preparation

The active substance and sodium chloride are dissolved in distilled water and then topped up to the volume given. The solution is sterilely filtered and transfered into 1 ml ampoules.
Sterilisation: 20 minutes at 120° C.

EXAMPLE IV

Suppositories containing 5 mg of 6-chloro-5,10-dihydro-5[(1-methyl-4-piperidinyl)acetyl]-11H-dibenzo[b,e][1,4]-diazepin-11-one

| Composition: | |
|---|---|
| 1 suppository contains: | |
| Active substance | 5.0 mg |
| Suppository mass | 1 695.0 mg |
| (e.g. Witepsol W 45 (R)) | 1 700.0 mg |

Method of preparation:

The finely powdered active substance is dispersed in the molten suppository mass which has been cooled to 40° C. At 37° C. the mass is poured into slightly chilled suppository molds.
Weight of suppository: 1.7 g

EXAMPLE V

Drops containing 6-chloro-5,10-dihydro-5-[(1-methyl-4-piperidinyl)acetyl]-11H-dibenzo[b,e][1,4]diazepin-11-one

| Composition: | |
|---|---|
| 100 ml of drops solution contain: | |
| Methyl p-hydroxybenzoate | 0.035 g |
| Propyl p-hydroxybenzoate | 0.015 g |
| Anise oil | 0.05 g |
| Menthol | 0.06 g |
| Pure ethanol | 10.0 g |
| Active substance | 0.5 g |
| Sodium cyclamate | 1.0 g |
| Glycerol | 15.0 g |
| Distilled water qs | 100.0 ml |

Method of preparation:

The active substance and sodium cyclamate are dissolved in about 70 ml of water and glycerol is added thereto. The p-hydroxybenzoates, anise oil and menthol are dissolved in the ethanol and this solution is added to the aqueous solution with stirring. Finally, the mixture is made up to 100 ml with water and filtered to remove any suspended particles.

The preceding specific embodiments are illustrative of the practice of the invention. It is to be understood, however, that other expedients known to those skilled in the art or disclosed herein, may be employed without departing from the spirit of the invention of the scope of the appended claims.

We claim:

1. A compound of the formula

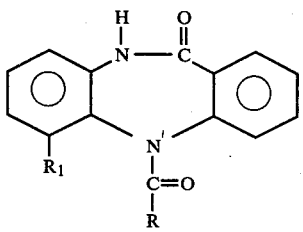

wherein R₁ is hydrogen or chlorine and R is (1-methyl-4-piperidinyl)-methyl, (1-methyl-1,2,5,6-tetrahydro-4-pyridinyl)-methyl, 1-methyl-1,2,5,6-tetrahydro-4-pyridinyl, (1-methyl-4-piperidinylidene)-methyl, (2,3-dehydro-8-methyl-8-azabicyclo[3,2,1]oct-3-yl)-methyl, (8-methyl-8-azabicyclo[3,2,1]oct]-3-ylidene)-methyl or an endo- or exo-(8-methyl-8-azabicyclo[3,2,1]oct-3-yl)-methyl, each being optionally substituted by one or two further methyls on the heterocyclic ring, a diastereomer or enantiomer thereof, or a non-toxic, pharmaceutically acceptable acid addition salt thereof.

2. A compound of claim 1, wherein R₁ is hydrogen or chlorine and R is (1-methyl-4-piperidinyl)-methyl, 1-methyl-1,2,5,6-tetrahydro-4-pyridinyl or endo-(8-methyl-8-azabicyclo[3,2,1]oct-3-yl)-methyl, or a non-toxic, pharmaceutically acceptable acid addition salt thereof.

3. A compound of claim 1 which is selected from the group consisting of 5,10-dihydro-5[(1-methyl-1,2,5,6-tetrahydro-4-pyridinyl)-carbonyl]-11H-dibenzo[b,e][1,4]diazepine-11-one and its non-toxic, pharmaceutically acceptable acid addition salts.

4. A compound of claim 1 which is selected from the group consisting of endo-5,10-dihydro-5-[(8-methyl-8-azabicyclo[3,2,1]-oct-3-yl)-acetyl]-11H-dibenzo[b,e][1,4]diazepin-11-one and its non-toxic, pharmaceutically acceptable acid addition salts.

5. 6-Chloro-5,10-dihydro-5-[(1-methyl-4-piperidinyl)acetyl]-11H-dibenzo[b,e][1,4]diazepin-11-one or a non-toxic, pharmaceutically acceptable salt thereof.

6. A pharmaceutical composition for preventing or treating ulcers in the stomach or intestines of warm-blooded animals which comprises an ulcergenically effective amount of at least one compound of claim 1 together with one or more inert carriers and/or diluents.

7. A method of inhibiting ulcers in warm-blooded animals comprising administering to warm-blooded animals an antiulcergenically effective amount of at least one compound of claim 1.

8. The method of claim 7, wherein R₁ is hydrogen or chlorine and R is selected from the group consisting of (1-methyl-4-piperidinyl)-methyl, 1-methyl-1,2,5,6-tetrahydro-4-pyridinyl and endo-(8-methyl-8-azabicyclo[3,2,1]oct-3-yl)methyl.

9. The method of claim 7, wherein the compound is selected from the group consisting of endo-5,10-dihydro-5-[(8-metyyl-8-azabicyclo[3,2,1]oct-3-yl)-acetyl]-11H-dibenzo[b,e][1,4]diazepin-11-one and its non-toxic, pharmaceutically acceptable acid addition salts.

10. The method of claim 7, wherein the compound is selected from the group consisting of 5,10-dihydro-5-[(1-methyl-1,2,5,6-tetrahydro-4-pyridinyl)-carbonyl]-11H-dibenzo[b,e][1,4]diazepine-11-one and its non-toxic, pharmaceutically acceptable acid addition salts.

11. The method of claim 7, wherein the compound is selected from the group consisting of endo-5,10-dihydro-5-[(8-methyl-8-azabicyclo[3,2,1]oct-3-yl)-acetyl]-11H-dibenzo-[b,e][1,4]diazepin-11-one and its non-toxic, pharmaceutically acceptable acid addition salts.

* * * * *

UNITED STATES PATENT AND TRADEMARK OFFICE
CERTIFICATE OF CORRECTION

PATENT NO. : 4,447,434

DATED : May 8, 1984

INVENTOR(S) : GÜNTER TRUMMLITZ et al.

It is certified that error appears in the above—identified patent and that said Letters Patent is hereby corrected as shown below:

Column 14, line 28, "66.05" should read -- C 66.05 --.

Column 15, line 34, the moiety "4diazepin" should read -- 4]diazepin --.

Column 20, line 45, "(50%)" should read -- (50% --.

Signed and Sealed this

Eighth Day of January 1985

[SEAL]

Attest:

*Attesting Officer*

GERALD J. MOSSINGHOFF

*Commissioner of Patents and Trademarks*